US010080815B2

(12) United States Patent
Cardinal et al.

(10) Patent No.: US 10,080,815 B2
(45) Date of Patent: Sep. 25, 2018

(54) SYSTEMS FOR DIFFUSING VOLATILE COMPOUNDS UTILIZING MOVEABLE PODS

(71) Applicant: The Dial Corporation, Scottsdale, AZ (US)

(72) Inventors: Keith Cardinal, Gilbert, AZ (US); Kevin Hafer, Chandler, AZ (US)

(73) Assignee: Henkel IP & Holding GmbH (DE)

( * ) Notice: Subject to any disclaimer, the term of this patent is extended or adjusted under 35 U.S.C. 154(b) by 160 days.

(21) Appl. No.: 14/982,938

(22) Filed: Dec. 29, 2015

(65) Prior Publication Data
US 2017/0182199 A1    Jun. 29, 2017

(51) Int. Cl.
*A61L 9/12* (2006.01)
*A01M 1/20* (2006.01)
*A01M 29/12* (2011.01)

(52) U.S. Cl.
CPC .............. *A61L 9/12* (2013.01); *A01M 1/2027* (2013.01); *A01M 29/12* (2013.01); *A61L 2209/133* (2013.01); *A61L 2209/134* (2013.01)

(58) Field of Classification Search
CPC .. A01M 1/2027; A01M 29/12; A01M 1/2044; A01M 1/2033; A01M 1/2055; A01M 7/0021; A61L 9/12; A61L 2209/133; A61L 2209/134; A61L 9/125; A61L 9/035; A61L 9/037; Y10S 261/88
USPC .......................................... 239/6, 52, 57–60
See application file for complete search history.

(56) References Cited

U.S. PATENT DOCUMENTS

| 5,050,798 | A |  | 9/1991 | Sullivan |
| 5,178,327 | A |  | 1/1993 | Palamand et al. |
| 5,695,692 | A |  | 12/1997 | Kennedy |
| 5,805,768 | A | * | 9/1998 | Schwartz .......... A61M 15/0045 261/DIG. 65 |
| 6,581,915 | B2 |  | 6/2003 | Bartsch et al. |
| 6,713,024 | B1 | * | 3/2004 | Arnell ..................... A61L 9/125 239/57 |
| 6,783,117 | B2 |  | 8/2004 | Wohrle |
| 6,834,847 | B2 |  | 12/2004 | Bartsch et al. |
| 6,950,607 | B2 |  | 9/2005 | Yip et al. |
| 7,011,795 | B2 |  | 3/2006 | Thompson et al. |
| 7,691,336 | B2 |  | 4/2010 | Westring |
| 7,734,159 | B2 | * | 6/2010 | Beland ..................... A61L 9/035 392/390 |

(Continued)

FOREIGN PATENT DOCUMENTS

WO    2004/105878 A1    12/2004
WO    2014/207273 A1    12/2014

*Primary Examiner* — Steven J Ganey
*Assistant Examiner* — Juan C Barrera
(74) *Attorney, Agent, or Firm* — P. Scott Smith

(57) ABSTRACT

A system for diffusing one or more volatile compounds includes a base and a pod tray, carried by the base. At least one pod is carried by the pod tray. The pod has a housing holding a volatile compound mass, the housing and mass being moveable relative to one another. An actuator is carried by the base, the actuator being operable to engage the pod and move the housing and the volatile compound mass relative to one another. The pod and the actuator are positionable relative to one another such that one or both of the pod and the actuator can be positioned proximate to one another to enable the actuator to engage the pod and move the housing and the volatile compound mass relative to one another.

12 Claims, 3 Drawing Sheets

(56) References Cited

U.S. PATENT DOCUMENTS

| | | | |
|---|---|---|---|
| 7,793,860 B2 * | 9/2010 | Bankers | A01M 1/2044 |
| | | | 206/223 |
| 7,942,388 B2 * | 5/2011 | Suissa | A61L 9/122 |
| | | | 239/59 |
| 8,016,207 B2 | 9/2011 | Kvietok et al. | |
| 8,170,405 B2 | 5/2012 | Harris | |
| 8,385,730 B2 | 2/2013 | Bushman et al. | |
| 8,483,553 B2 | 7/2013 | Tollens et al. | |
| 2002/0179728 A1 * | 12/2002 | Beidokhti | A01M 31/008 |
| | | | 239/6 |
| 2003/0175148 A1 | 9/2003 | Kvietok et al. | |
| 2005/0205916 A1 * | 9/2005 | Conway | A61L 9/127 |
| | | | 257/299 |
| 2006/0081721 A1 | 4/2006 | Caserta et al. | |
| 2009/0212124 A1 | 8/2009 | Kenny | |
| 2013/0334336 A1 | 12/2013 | Haran et al. | |

* cited by examiner

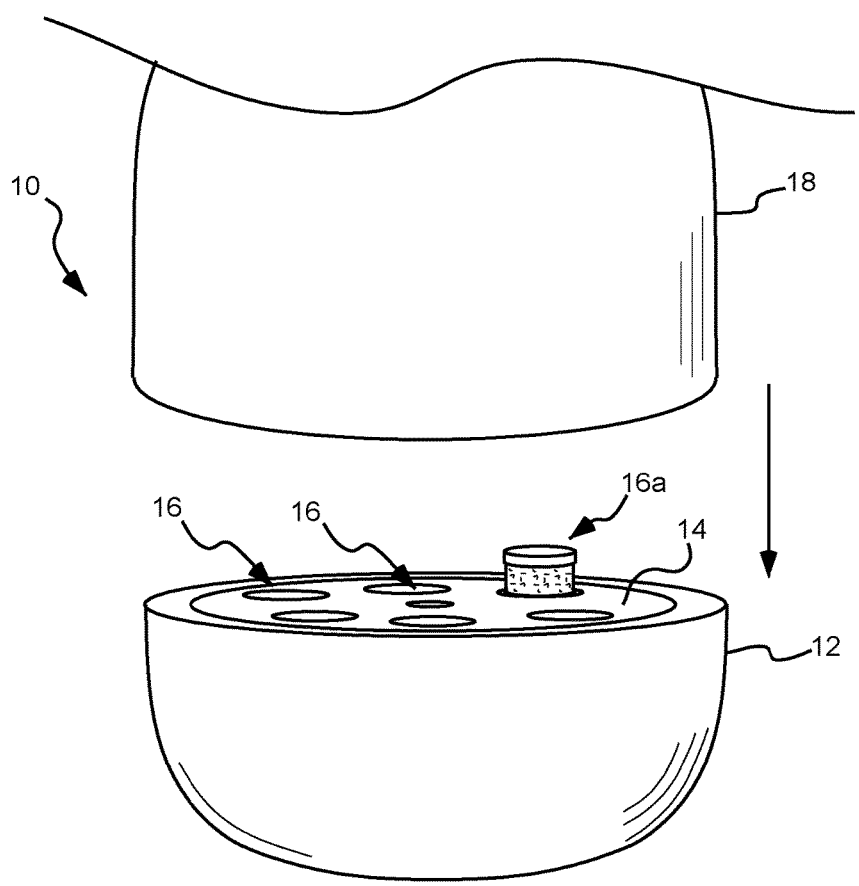
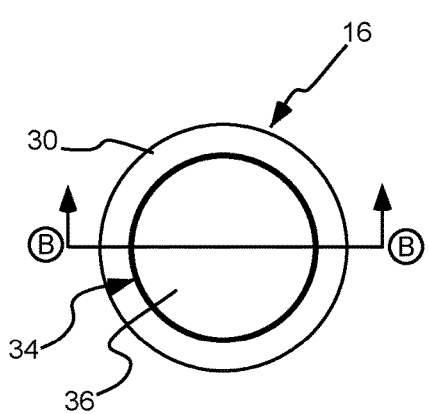
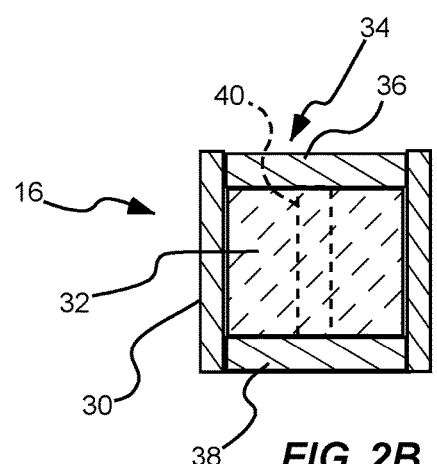
FIG. 1
FIG. 2A
FIG. 2B

• # SYSTEMS FOR DIFFUSING VOLATILE COMPOUNDS UTILIZING MOVEABLE PODS

BACKGROUND OF THE INVENTION

Field of the Invention

The present invention relates generally to systems for diffusing volatile compounds such as fragrant materials, disinfectants and pesticides.

Related Art

There exist a variety of systems that cause volatile compounds to be diffused into an environment. One such example is the well-known air freshener that releases scented materials to freshen the air of homes, vehicles, offices and the like. Air fresheners such as this can be as simple as cardstock impregnated with a volatile compound, or as sophisticated as electronic systems that selectively release measured quantities of liquefied compounds at varying frequency and potency.

While many such systems exist, they generally suffer from significant loss of performance over time, or they are so complex that cost considerations become prohibitive, or both. For at least these reasons, designers continue to seek solutions to simplify operation of such systems while maintaining superior performance.

SUMMARY OF THE INVENTION

In accordance with one aspect of the invention, a system is provided for diffusing one or more volatile compounds included in a volatile compound mass. The system can include a base and a pod tray, carried by the base. At least one pod can be carried by the pod tray, the pod having a housing holding a volatile compound mass. The volatile compound mass and the housing can be moveable relative to one another, whereby moving the housing and the volatile compound mass relative to one another causes a volatile compound to be diffused. An actuator can be carried by the base, the actuator operable to engage the pod and move the housing and the volatile compound mass relative to one another. The at least one pod and the actuator can be positionable relative to one another such that one or both of the pod and the actuator can be positioned proximate to one another to enable the actuator to engage the pod and move the housing of the pod and the volatile compound mass relative to one another to thereby diffuse the volatile compound.

In accordance with another aspect of the invention, a system is provided for diffusing one or more volatile compounds included in a volatile compound mass. The system includes a base and a pod tray, carried by the base. One or more pods can be carried by the pod tray, the pods each having a housing holding a volatile compound mass. The volatile compound mass and the housing can be moveable relative to one another, whereby moving the housing and the volatile compound mass relative to one another causes a volatile compound to be diffused. Each of the pods can have an actuating surface associated therewith. A sloped ramp can be carried by the base. Movement of the pod tray relative to the base can cause the actuating surface of the pods to engage the sloped ramp to cause the housing and the volatile compound mass of the pods to move relative to one another.

In accordance with another aspect of the invention, a method is provided of diffusing a volatile compound included in a volatile compound mass within a housing of a pod, the housing of the pod including a sloped ramp associated therewith and the pod having an actuating surface associated therewith. The method can include positioning the pod and the sloped ramp in proximity with one another, and moving the pod and the sloped ramp relative to one another to thereby cause the actuating surface of the pod to track along the sloped ramp to thereby move the housing of the pod relative to the volatile compound mass to thereby diffuse a volatile compound.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 1 is a perspective view of a volatile compound diffusing system in accordance with an embodiment of the invention;

FIG. 2A is a top view of a diffusion pod in accordance with an embodiment of the invention;

FIG. 2B is a side, sectioned view of the diffusion pod of FIG. 2A, taken along section B-B of FIG. 2A;

DETAILED DESCRIPTION

Figure 3:
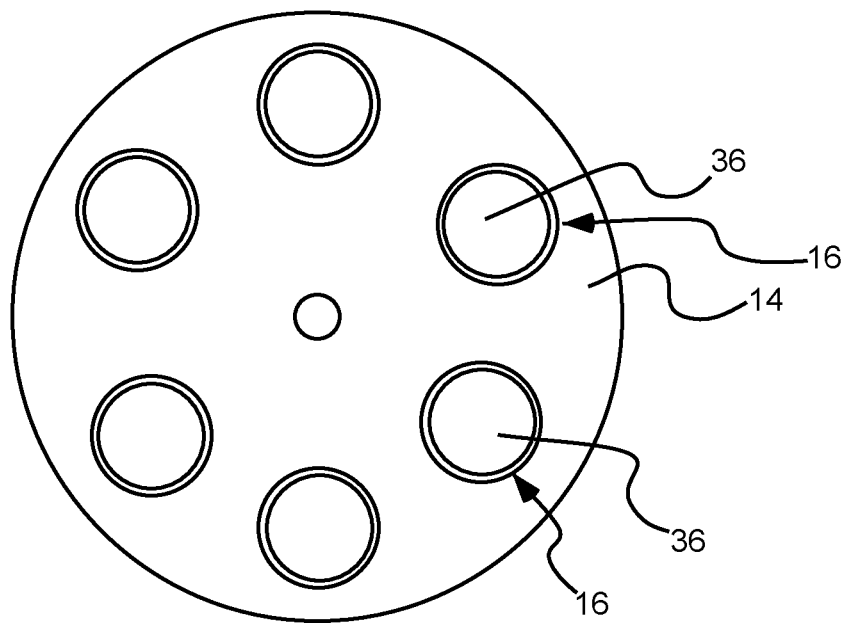
FIG. 3 is a top view of a pod tray carrying a series of pods in accordance with an embodiment of the invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to "a diffusion pod" can include one or more of such pods, if the context dictates.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms are sometimes used herein to describe and claim various components of the diffusion systems of the present invention. Such terms include, without limitation, "upward," "downward," "horizontal," "vertical," etc. These terms are generally not intended to be limiting, but are used to most clearly describe and claim the various features of the invention.

Where such terms must carry some limitation, they are intended to be limited to usage commonly known and understood by those of ordinary skill in the art having possession of this disclosure. For example, the directional terms can be used herein to describe various aspects of the present volatile composition diffusion systems in the case where the diffusion systems are used as a tabletop application. One of ordinary skill in the art will appreciate that the present systems can be used in a variety of other orientations, such as wall-mounted units or ceiling-mounted units. In these cases, the directional terms will, of course, apply differently to the system. One of ordinary skill in the art having possession of this disclosure will readily appreciate the adaptability of such words to varying orientations of the present technology.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology provides systems and methods for controllably releasing various volatile compounds into an environment. Such volatile compounds can include, without limitation, fragrant materials, pesticides, pest repellants, disinfectants, etc. In the interest of clarity, much of the discussion below will focus on the use of the technology to deliver fragrant material, as an air freshener. It is, however, to be understood that the present invention is not limited to such applications and can be utilized in a variety of air treatment regimes in various environments.

Traditional air fresheners are well known and used by many people to treat the air in a home, vehicle or place of business. One primary limitation of these traditional air fresheners is the loss of performance, either real or perceived, over time. Most delivery mechanisms exhibit a noticeable decay in the amount of fragrance that is being delivered over time. To compound this issue, most consumers will also begin to become anosmic to the fragrance after a short period of time, which limits the consumer's ability to appreciate the fragrance. This leads to the perception that air fresheners only last a short period of time, when in reality they may continue to deliver fragrance for much longer. Some devices have attempted to counter one or both of these issues by focusing on linear fragrance delivery, or by alternating between fragrances to address anosmia. However, these devices are very complicated and expensive, so there remains an unmet need for simple and low-cost devices that can address these issues.

The present technology provides a simple device that utilizes very little power to periodically activate a new fragrance on a selectable time interval with no interaction required from the user. This device enables the consumer to load a custom combination, or "playlist," of their favorite fragrances, which can then be activated over time to maintain a fresh fragrance experience by intermittently changing the fragrance. The present systems use a very simple and efficient motion that enables the devices to use very little power and is accordingly very simple to operate.

FIG. 1 illustrates a system 10 for diffusing one or more volatile compounds. The system includes a base 12 and a cover 18, removably positionable on the base. The cover 18 can include one ore more openings (not shown) that allow the volatile material, once released from the pods, to leave the system and enter the surrounding environment. A pod tray 14 can carry a plurality of diffusion pods 16. A single pod 16a is shown in FIG. 1 extending exposed from the pod tray 14, with the remaining pods lying dormant in the view shown. During operation, the system selectively activates one or more pods by raising the pod or pods into the position shown by pod 16a. Once in this position, the volatile compound included in the volatile compound mass present in the pod is released into the environment.

Activation of the pods 16 is discussed in more detail below. Generally speaking, however, the term "activation" is used herein to describe a condition in which volatile compounds included in a volatile compound mass are allowed to diffuse into a surrounding environment. In the case of the pods shown in the figures, this typically involves moving some structure relative to another such that a volatile compound mass that was previously contained in a sealed closure is exposed to the surrounding environment. Exposure of the volatile compound mass results in diffusion of volatile compounds included in the mass.

The system 10 can advantageously be configured to allow a user to load into the pod tray 14 the scents he or she wishes to experience, by selecting from various pods 16 made available to the consumer. In one example, the system 10 can be provided to the consumer with a variety of disposable pods. The consumer can then select which pods he or she wishes to use, and load those pods into the device. Alternately, the pods could be pre-loaded and the system can be provided to a consumer in a ready-to-use condition.

Figure 5:
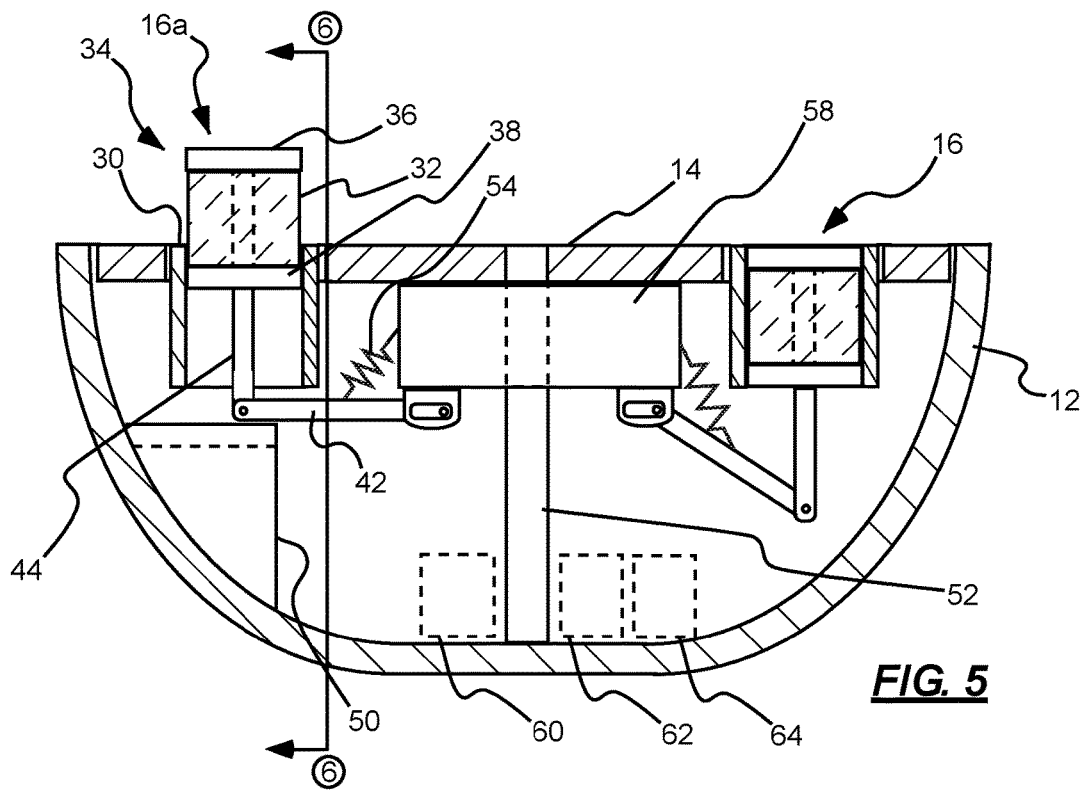
FIG. 5 is a side, partially sectioned view of the volatile compound diffusing system of FIG. 1.
Figure 6:
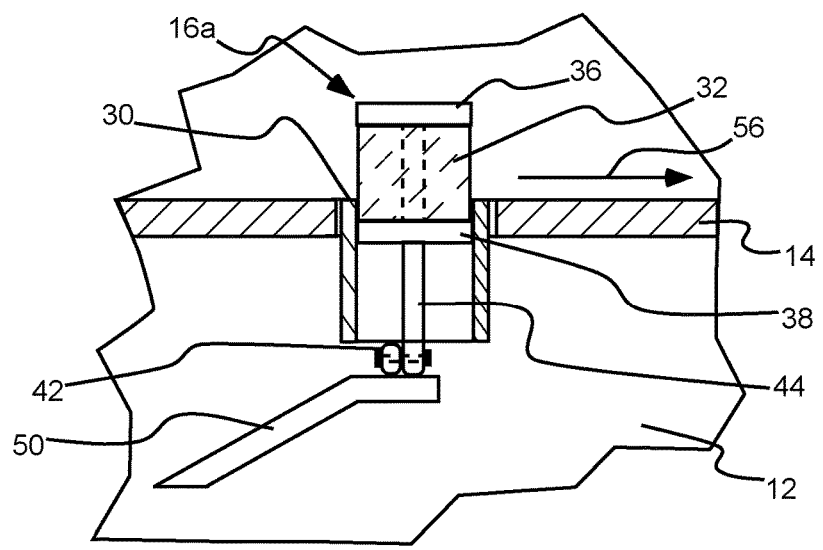
FIG. 6 is a more detailed view of a portion of the diffusing system of FIG. 5, taken along section 6-6 of FIG. 5.

As shown in FIGS. 2A and 2B, in one embodiment the pod 16 can include a generally cylindrical housing 30 within which a spindle 34 can be slidably received. Spindle 34 can include a cap 36, a base 38 and, optionally, a connecting member 40. A volatile compound mass 32 can be carried by the spindle. In one embodiment, the mass 32 is formed as a toroid that circumscribes the connecting member 40. In FIG. 2B, the pod is shown in a closed or sealed configuration. In this state, the volatile compounds included in the volatile compound mass are sealed within the housing and are thus prevented from diffusing. Pod 16a of FIGS. 1, 5 and 6 is shown in an extended, or activated position. In this position, the spindle 34 has been moved longitudinally relative to the housing 30, which exposes the volatile compound mass 32 to the environment, allowing the volatile compounds contained in the mass to be diffused.

The configuration of the pod 16 is advantageous in that the pod can be selectively activated and deactivated. When in the closed configuration, cap 36 and base 38 function to seal the volatile compound mass 32 within the housing 30. During activation, the volatile compound mass can be exposed for a desired period of time, thereby diffusing a volatile compound. After activation, the pod can be closed again by retracting it into the housing. In this manner, any volatile compound not initially diffused can be used at a later time by again moving the spindle out of the housing. While not so required, it is contemplated that the pods can initially be sealed with a frangible seal (not shown) that can be compromised when the pod is initially activated. In this manner, the pods can be stored for relatively long periods of time before an initial use.

The volatile compound mass 32 can be formed from a variety of materials. Suitable compositions include, without limitation, scented aqueous gels, scented non-aqueous gels, waxes, permeable membranes, or fragrance-infused absorbent material such as paper, fibrous masses, ceramic, porous plastic, wood, or inorganic porous solids (i.e. salt), etc. Generally, exposure of the volatile compound mass to the environment results in one or more volatile compounds being released into the environment to act as a fragrant agent, insecticide, pesticide, repellant, disinfectant, etc. In the examples shown in the present disclosure, the mass 32 is at least partially solid, so that it retains its shape independently of the structure containing the mass.

Figure 4:
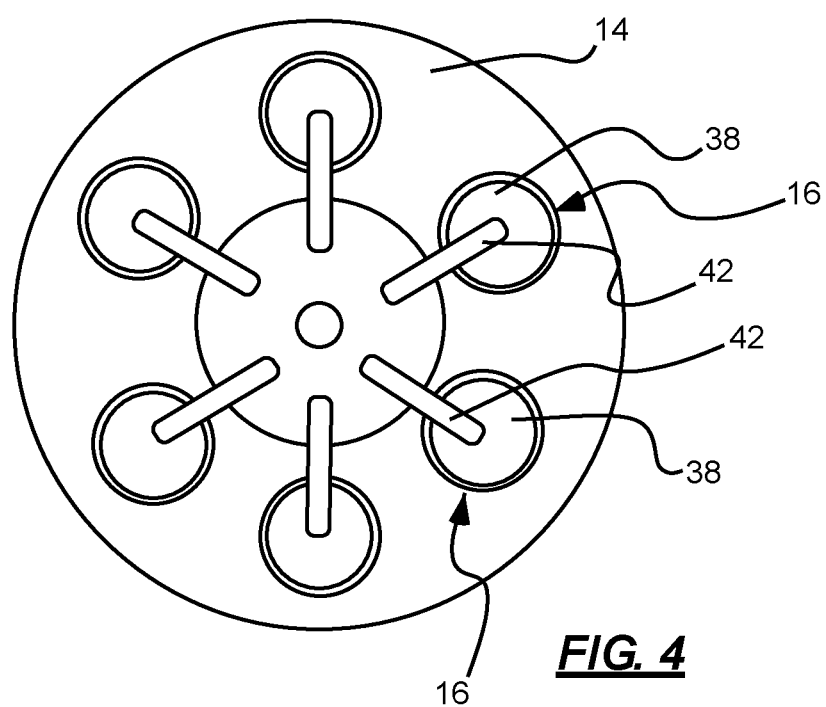
FIG. 4 is a bottom view of the pod tray and pods of FIG. 3.

FIGS. 3 and 4 illustrate a series of pods 16 installed within a pod tray 14. While six pods are illustrated in the figures, it is to be understood that the system can include as few as one pod, or as many pods as can functionally be accommodated by the base 12. Also, while the pod tray is illustrated as a generally planar structure including a series of openings to receive pods, the tray can be formed from a variety of structural elements that accomplish the same function. For example, a frame-like structure can be utilized that can carry one or more pods without requiring a planar receiver.

As shown in FIGS. 4-6, each pod 16 can include an extension arm 42 associated therewith. In the examples shown, the extension arm is coupled (indirectly, in this case) to the base 38 of the spindle of the pod. The extension arm can aid in activating the pod by moving the pod relative to the housing. As shown in FIG. 5, the extension arm can be coupled to lifting arm 44, which in turn is coupled to the base 38. As the extension arm is moved upwardly or downwardly, the lifting arm is correspondingly moved, which results in movement of the spindle 34 relative to the housing 30.

Movement of the extension arm 42 or lifting arm 44 can be achieved in a variety of manners. In the example shown in FIGS. 5 and 6, the base 12 includes a sloped ramp 50 along which the lifting arm or extension arm can track. Pod 16a is shown in FIGS. 1, 5 and 6 in an activated state. In this example, base 38 of pod 16a is coupled to lifting arm 44, which is in turn coupled to extension arm 42. Pod tray 14 is rotationally moved relative to the base, as shown by directional indicator 56 (FIG. 6). As the pod tray rotates, the lifting or extension arm contacts and tracks along ramp 50. As the tray rotates to the right of FIG. 6, the lifting or extension arm is forced upwardly. This results in the base 38 of the pod being forced upward, which in turn exposes the volatile compound mass 32 to the environment, diffusing the volatile compound included therein.

The system can be maintained in the position shown in FIG. 6 as long as it is desired to expose the volatile compound mass 32 to the environment. When it is desired to deactivate the pod 16a, the tray 14 can be further rotated in direction 56, and as the lifting arm 44 or extension arm 42 passes to the right of the ramp, the base 38 can retract into the housing 30 at which point cap 36 again seals the volatile compound mass within the housing.

The system can include a biasing element or spring, shown schematically at 54 in FIG. 5, coupled between the extension arm 42 and another component of the system. In the example shown, the spring is coupled to rotational platform 58, discussed in more detail below. The biasing element or spring can force the extension arm 42 downwardly once the pod no longer engages the ramp 50, to aid in retracting the volatile compound mass into the housing. In addition to lifting and lowering the base 38, the extension arm 42 and lifting arm 44 also aid in retaining the spindle 34 within the housing 30. Thus, the base, the cap and the volatile compound mass are prevented from being inadvertently expelled from the unit when raised by the ramp 50.

The lifting arm 44, extension arm 42 and biasing element or spring 54 are illustrated in the figures for exemplary purposes only. It is to be understood that the arrangement by which the spindle 34 is moved relative to the housing 30 can be accomplished in a number of manners. For example, the lifting arm and extension arm can be an integral unit, formed from a pliable material that provides sufficient flexibility to perform the functions shown. The spring can be positioned differently than shown, or can be omitted. Also, the lifting and extension arm can be omitted, and the actuating surface that contacts the ramp can be a portion of the pod, or another type of structure extending from the pod.

During operation of the system, the pod tray 14 is moved to a desired position in which a particular pod 16 can be activated. After being moved into this position (or during the positioning), the pod is activated to release one or more volatile compounds. It is to be understood that the underlying relative movement required to position and activate any given pod can be achieved in a variety of manners. The pod tray 14 can rotate relative to the base 12 (or ramp 50), or the base or ramp can rotate relative to the pod tray, or both. In addition to the use of rotational movement, the activation can be achieved by utilizing relative linear motion, and any combination of the two.

Rotation of the base 12 and pod tray 14 relative to one another can be performed in a variety of manners. In the example shown in FIG. 5, a rotational platform 58 can be rotationally coupled to an upright 52. The pod tray 14 can be coupled to the rotational platform. The rotational platform can be rotated by way of a motor 60, which can be driven by a power source 62 and controlled by a regulator/controller 64. The motor 60 can be any of a variety of available motors capable of producing the movement described.

The power source 62 can vary, as well. In one aspect of the invention, the system can be powered by mechanical power, delivered, for example, by a "wind-up" mechanism that stores energy in the form of springs and/or similar components. Such mechanisms are known for use in analogous applications, such as timepieces, animatronics, toys, etc. Alternately, a DC battery power source can be used, as can available household AC current.

The controller/regulator 64 can provide flexible functionality to the system. The controller can activate the motor for a particular duration and at a particular speed, until, for example, a particular pod is activated. After this period, the controller can maintain the position of the pod to allow some or all of the volatile compound to be diffused, then activate the motor again to move the system to activate an additional pod. A program to control such operation can be selected, for example, to activate a certain pod for one week, after which another pod could be activated for another week, etc. Any of a myriad of activation frequency and/or duration cycles can be achieved.

The power 62, control 64 and motor 60 functions can vary widely, as is best suited for any particular application. While detailed examples of such systems are omitted from this disclosure, one of ordinary skill in the art having possession of this disclosure could readily adapt the current technology for use with any such power and control systems.

Activation of the pods (e.g., movement of the pod housing relative to the volatile compound mass) is shown herein by the use of a ramp, along which some actuating surface of the pod tracks (or a structure connected to the pod, such as the lifting or extension arm). Thus, activation is shown through the use of relative motion of some surface along a sloped ramp. It is to be understood, however that activation of the pods can be achieved in a variety of other manners. For example, one or more linear actuators can be used to move the volatile compound mass relative to the housing, or vice versa.

Also, while the examples shown actuate a single pod, in one embodiment, the system can activate two or more pods simultaneously. For example, a second ramp can be carried by the base, which can activate a second pod during movement of the pod tray.

In addition to the structural components discussed above, the present invention also provides various methods of diffusing volatile compounds included in the volatile compound mass present in a pod, methods of installing diffusion pods within an activation system, and methods of treating or conditioning an environment with volatile compounds.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

We claim:

1. A system for diffusing one or more volatile compounds included in a volatile compound mass, the system comprising:
    a base;
    a pod tray, carried by the base;
    at least one pod carried by the pod tray, the at least one pod having a housing holding a volatile compound mass, the volatile compound mass and the housing being moveable relative to one another, whereby moving the housing and the volatile compound mass relative to one another causes a volatile compound to be diffused; and
    an actuator, carried by the base, the actuator operable to engage the at least one pod and move the housing and the volatile compound mass relative to one another;
    the at least one pod and the actuator being positionable relative to one another such that one or both of the at least one pod and the actuator can be positioned proximate to one another to enable the actuator to engage the at least one pod and move the housing of the at least one pod and the volatile compound mass relative to one another to thereby diffuse the volatile compound, wherein the actuator includes a sloped ramp along which an actuating surface associated with the at least one pod tracks while the at least one pod and the actuator move relative to one another and a spindle, slidably received within the housing, the spindle including a base and a cap, the volatile compound mass carried between the base and the cap.

2. The system of claim 1, wherein the at least one pod tray is moveable relative to the base, and wherein the actuator is stationary relative to the base.

3. The system of claim 2, wherein the at least one pod tray is rotatably moveable relative to the actuator.

4. The system of claim 1, wherein the actuating surface associated with the at least one pod includes an extension arm coupled to the base of the spindle.

5. The system of claim 4, further comprising a plurality of pods, each of the pods including an extension arm coupled to a base of a spindle.

6. The system of claim 4, further comprising a biasing element coupled to the extension arm, the biasing element returning the at least one pod to an initial configuration after activation of the at least one pod.

7. The system of claim 1, further comprising a motor powered by an energy source, the motor operable to move the pod tray relative to the actuator.

8. The system of claim 7, further comprising a regulator, operably coupled to the motor, the regulator operable to allow a user to control one of: activation frequency and activation duration of the at least one pod.

9. A system for diffusing one or more volatile compounds included in a volatile compound mass, the system comprising:
    a base;
    a pod tray, carried by the base;
    one or more pods carried by the pod tray, the pods each having a housing holding a volatile compound mass, the volatile compound mass and the housing being moveable relative to one another, whereby moving the housing and the volatile compound mass relative to one another causes a volatile compound to be diffused;
    each of the one or more pods having an actuating surface associated therewith;
    a sloped ramp, carried by the base; and
    a spindle, slidably received within the housing, the spindle including a base and a cap, the volatile compound mass carried between the base and the cap
    wherein movement of the pod tray relative to the base causes the actuating surface of the one or more pods to engage the sloped ramp to cause the housing and the volatile compound mass of the one or more pods to move relative to one another.

10. The system of claim 9, wherein the actuating surface associated with the one or more pods includes an extension arm coupled to the base of the spindle.

11. The system of claim 10, further comprising a plurality of pods, each of the pods including an extension arm coupled to a base of a spindle.

12. The system of claim 10, further comprising a biasing element coupled to the extension arm, the biasing element returning the one or more pods to an initial configuration after activation of the one or more pods.

\* \* \* \* \*